United States Patent [19]

Clayton et al.

[11] 4,278,882

[45] Jul. 14, 1981

[54] COAL ASH MONITORS

[75] Inventors: Colin G. Clayton; Malcolm R. Wormald, both of Abingdon, England

[73] Assignee: United Kingdom Atomic Energy Authority, London, England

[21] Appl. No.: 80,006

[22] Filed: Sep. 28, 1979

[30] Foreign Application Priority Data

Oct. 2, 1978 [GB] United Kingdom ............... 39011/78

[51] Int. Cl.³ .................... G01V 5/00; G01N 23/00; G06K 9/00
[52] U.S. Cl. .................................. 250/255; 250/359; 340/146.3 K
[58] Field of Search ................... 250/255, 270, 358 R, 250/359, 360; 246/167 R, 182 B, 249; 340/146.3 K

[56] References Cited

U.S. PATENT DOCUMENTS

| 3,016,456 | 1/1962 | Corporon | 246/249 |
| 3,132,247 | 5/1964 | Wright | 250/359 |
| 3,974,992 | 8/1976 | Matty | 246/182 B |
| 4,066,892 | 1/1978 | Givens | 250/270 |

Primary Examiner—Alfred E. Smith
Assistant Examiner—Janice A. Howell
Attorney, Agent, or Firm—Larson, Taylor and Hinds

[57] ABSTRACT

A monitor for determining the ash content of coal in wagons consisting of a structure including means for irradiating each wagon as it passes the structure with a known dose of neutrons, means for detecting and measuring the intensities of γ-rays emitted by ash-forming elements in the coal, and means for providing an indication of the concentration of the ash-forming elements. There also are included interlocks for ensuring that the neutron source is only operated when a loaded wagon is in the appropriate position.

18 Claims, 3 Drawing Figures

COAL ASH MONITORS

The present invention relates to the measurement of the ash content of coal, and more specifically to the measurement of the ash content of coal contained in transport containers such as railway wagons as they are supplied to a power station.

A high ash content in the coal supplied to a power station can cause the boilers to fail, resulting in expensive repairs being necessary and a loss in generating capacity while repairs are being carried out. The quality of the coal supplied to a power station can vary in a random fashion, for example, due to failures in the washing plant at the colliery whence the coal has come. It is highly desirable therefore, to be able to monitor the ash content of the coal before it is unloaded at the power station in order that poor quality coal having a high ash content can be prevented from reaching the boilers of the power station.

It has been found that the ash-forming properties of coal are related to the concentration of compounds containing certain elements such as iron, silicon or aluminium, and hence the ash content of the coal can be estimated by measuring the concentration of one or more of these elements in the coal.

Various methods have been proposed for the on-stream analysis of coal, but these techniques have not proved to be satisfactory for use with coal while it is still in the containers in which it has been transported to the power station so that poor quality coal can be isolated and rejected before it is unloaded at the power station. For example, methods of analysis which rely on the scattering of low-energy X-rays are not satisfactory because such X-rays have only a limited depth of penetration in coal, and could not penetrate the sides of the containers for the coal, be they railway wagons or larger lorries. Methods based on the absorption of $\gamma$-rays or neutrons are not specific to the elements one would be interested in determining. Sampling methods are possible, but these are slow and have their own problems of ensuring that the sample is representative and firmly identified with its source, and that the analysis can be done in time to prevent any given load of coal which is found to be of poor quality from being unloaded.

According to the invention there is provided an apparatus for measuring the ash content of coal contained in a transport container, comprising means for irradiating a known quantity of coal in a transport container with a known dose of neutrons, means for detecting $\gamma$-rays having a predetermined energy emitted by the irradiated coal, the $\gamma$-rays being indicative of the presence of an ash-forming element in the coal, means for producing a signal related to the intensity of the $\gamma$-ray emission from the irradiated coal, and means responsive to the said signal to provide an indication of the concentration of the ash-forming element in the coal.

There may also be provided means for identifying and isolating transport containers containing coal the ash content of which exceeds a specified level.

The means for irradiating the coal with neutrons may be positioned so as to irradiate the coal from above, below, or through the side of the transport container. The preferred arrangement is so as to irradiate the coal from the side at a level low down at the side of the transport container. Such an arrangement ensures that the portion of the coal which is irradiated is spatially well defined, and is representative of the bulk of the coal in the transport container.

Preferably the apparatus includes means for ensuring that the means for irradiating the coal with neutrons is only operative when a transport container containing coal is in the path of neutrons emitted by the means for irradiating the coal with neutrons.

There may also be provided means for measuring the thickness of the wall of the transport container, means for estimating the moisture content of the coal, and means for measuring the background intensity of $\gamma$-rays of the predetermined energy and means for determining the bulk density of the coal in order to enable allowance to be made for variations in these parameters.

In one form of neutron irradiating means there is provided a neutron source, a radiation shield isolating the neutron source and means for exposing the neutron source in response to a signal from a detector that a transport container is in a position suitable for the coal in the transport container to be irradiated by neutrons from the neutron source.

The detector may comprise a photo-electric device or a pressure-sensitive device which is activated when a load corresponding to a full transport container is upon it.

Suitable neutron sources are $^{252}$Cf, $^{241}$Am/Be, or other ($\alpha$,n) sources or ($\gamma$,n) sources, or an electron tube source which produces neutrons at an energy of about 14 MeV. Such a tube source can be arranged to be operated continuously or in a pulsed mode whenever a coal-containing transport container is in a suitable position for its contents to be irradiated with neutrons from the source.

If desired, for example to achieve greater accuracy, the $\gamma$-ray detecting means may be adapted to detect and measure $\gamma$-rays of more than one energy, each of the $\gamma$-rays arising from a selected ash-forming element. For example, the apparatus can be adapted to measure the concentration of aluminium or silicon in the coal alone, or the concentrations of aluminium and silicon in the coal together.

In a preferred form of the invention, the transport containers are wagons in a train, the irradiating means is positioned at the trackside so as to irradiate the coal under test through the sides of the wagons, the $\gamma$-ray detector is positioned at a known distance from the irradiating means, the coal wagons are caused to traverse the length of track including the irradiating means and the $\gamma$-ray detector at a known steady speed. Thus it is possible to estimate the volume of coal which is irradiated with neutrons, the dose received, the elapsed decay time and the total amount of $\gamma$-activity from the ash-forming element, or elements. From this information the indication of the concentration of the ash-forming element, or elements, is derived.

The invention will now be explained, by way of example, with reference to the accompanying drawings, in which.

Figure 1:
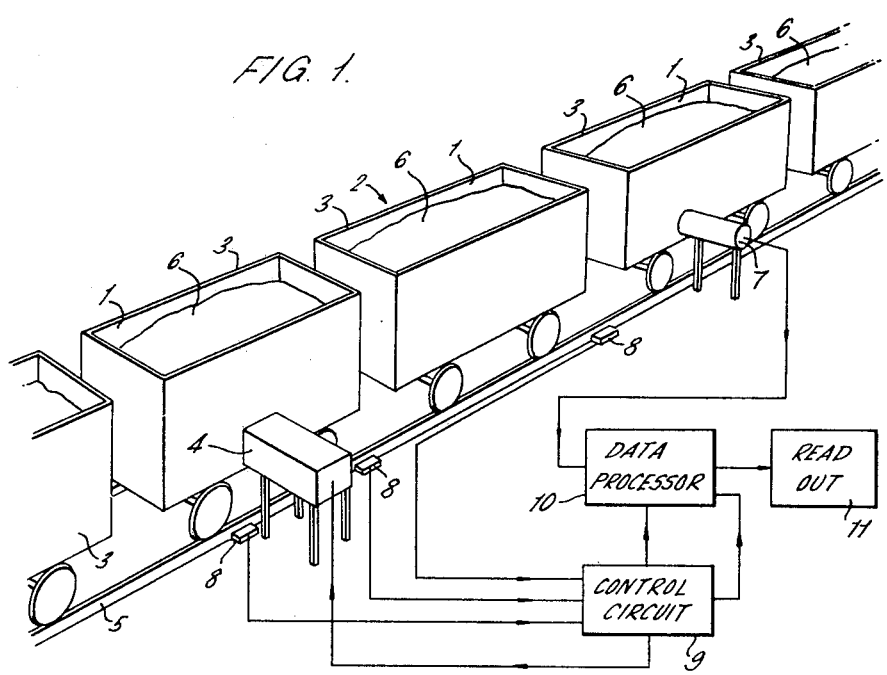
FIG. 1 is a schematic drawing of a system embodying the invention for monitoring the ash content of coal being delivered by train to a power station.

Referring to FIG. 1 of the drawings which illustrate a system for measuring the aluminium content of coal as an indication of the ash content, a portion of a train of coal wagons 1 is indicated by the numeral 2. The coal wagons 1 are made of iron and have side walls 3 made of iron sheets some 5/32 of an inch thick. A neutron source assembly 4 is positioned by the side of the track 5 on which the train 2 is running. The neutron source assembly 4 is positioned so as to irradiate the coal 6 in the wagons 1 through the walls 3 of the wagons 1 at a position well below the top of the coal 6. Some hundred yards down the track 5 from the position of the neutron source 4 there is positioned a γ-ray detector assembly 7 which is such as to produce an electrical signal indicative of the total γ-ray activity of the coal 6 in each wagon 1 as it passes the γ-ray detector assembly 7. Also positioned along the side of the track 5 are three sensors 8. The sensors 8 are pressure-sensitive and produce signal pulses when loads exceeding a minimum value which corresponds to the axle weight of a loaded coal wagon 1 pass over them. One sensor 8 is used to detect the presence of a coal wagon 1 in an operative position in relation to the neutron source assembly 4. The two remaining sensors 8 are separated by a known distance and are used to measure the speed of the train 2. The signals from the sensors 8 are fed to a control circuit 9 which produces a neutron source control signal which is applied to the neutron source assembly 4, a train speed data signal and a data processing control signal, both of which are applied to a data processing circuit 10. The signal from the γ-ray detector 7 assembly also is applied to the data processing circuit 10. After processing, a final output signal representative of the concentration of one or more ash-forming elements in the coal is produced and displayed by a read-out device 11.

There can also be included a further sensor which is adapted to react to the passage of the first axle of a locomotive hauling the coal wagons 1 to initially switch on the apparatus.

The neutron source assembly 4 is arranged to produce thermal neutrons of an energy such as to be captured by the $^{27}$Al isotope, resulting in the production of $^{28}$Al and the subsequent emission of γ-rays with an energy of 1.7 MeV.

Figure 2:
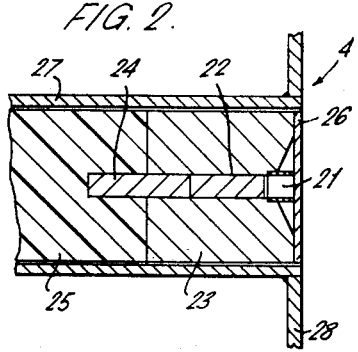
FIG. 2 is a cross-section of a neutron source assembly for use in the embodiment of FIG. 1.

Referring to FIG. 2 of the drawings, the neutron source assembly 4 consists of a source capsule 21, which contains a nominal 200 μg of $^{252}$Cf having a total neutron output of $4.7 \times 10^8$ neutrons an hour, mounted in a bore 22 in a cylindrical lead housing 23. The source capsule 21 is held in place by means of a lead support 24, which in turn is attached to a high-density polythene push rod 25, and an aluminium retaining plate 26. The lead housing 23 is mounted within a polythene-lined steel pipe 27 which is welded through the centres of opposite ends of a water filled tank, of which only a part 28 is shown. The water tank has dimensions of 4 ft × 4 ft × 6 ft. A mechanism, which is not shown, is arranged to move the push rod 25 in response to the neutron source control signal from the control circuit 9 so as to move the source capsule 21 from a storage position half-way along the steel pipe 27 to an operative position where the aluminium retaining plate 26 is flush with the wall 28 of the water tank.

The entire assembly is placed so that in the operative position the source capsule is about 1 ft from the sides 3 of the wagons 1 as they pass the source assembly 4.

It has been found that when the source capsule 21 is in the storage position, the radiation level at about 1 ft from the water tank is less than 2.5 mR/hour. The radiation is almost entirely due to γ-radiation from neutron capture by hydrogen. If desired, this radiation level can be reduced by adding boron to the water.

Other materials which produce neutrons of suitable energies are $^{241}$Am/Be, or other (α,n) sources, or a 14 MeV electron tube source. If an electron tube source is used, it can either be operated continuously, in which case it will have to be exposed in an intermittent way such as has been described already, or it can be operated in a pulsed mode in response to the neutron source control signal from the control circuit 9.

The separation between the neutron source assembly 4 and the γ-ray detector assembly 7 is not critical. Indeed, if it is desired to detect and measure prompt γ-rays, the separation between the neutron source assembly 4 and the γ-ray detector assembly 7 can be as little as 3 feet.

Figure 3:
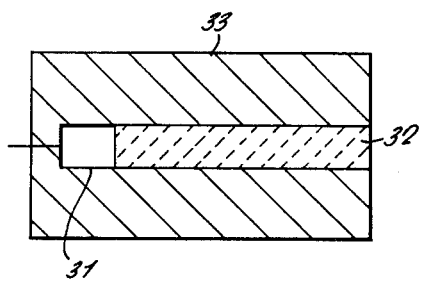
FIG. 3 is a cross-section of a $\gamma$-ray detector assembly for use in the embodiment of FIG. 1.

Referring to FIG. 3, the γ-ray detector assembly 7 consists of a sodium iodide γ-ray detector 31 with a crystal 32 some 76 mm diameter by 76 mm long mounted with its axis horizontal, and at the same height as the source capsule 21 of the neutron source assembly 4. The detector 31 is mounted in a lead housing 33 to screen the crystal 32 from extraneous radiation. The housing 33 is mounted on a stand (not shown) so that the crystal 32 is approximately the same distance from the walls 3 of the wagons 1 as is the source capsule 21 of the neutron source assembly 4 when it is in its operative position. Other forms of detector for γ-rays having energies > 50 keV can be used.

If desired, a measurement of the background activity can be made by means of a second identical γ-ray detector assembly positioned the same distance up-line of the neutron source assembly 4 as the γ-ray detector assembly 7 is downline of the neutron source assembly 4 and arranged to generate a correcting signal, which also is applied to the data processing circuit 10. Other parameters which can be monitored, and for which correcting signals can be generated and applied to the data processing circuit 10, are the actual thickness of the walls 3 of the wagons 1, the moisture content of the coal 6 in the wagons 1, and the bulk density of the coal.

The last can be determined by measuring the intensity of the 2.23 MeV γ-rays arising from thermal neutron capture in hydrogen. For this purpose the γ-ray detector assembly 7 can include a detector for the appropriate γ-rays located close to the neutron source assembly 4 at the same height and at the same distance from the sides of the wagons 1. The 2.3 MeV γ-rays detector should be suitably shielded from γ-rays arising from the material shielding the neutron source 21.

Also, if desired, the data processing circuit 10 can be made to operate a warning device if the ash content of the coal rises above a specified level. Furthermore the data processing circuit 10 can be made to actuate some means of diverting wagons 1 which contain faulty coal into a siding so that they are not presented to the unloading equipment of the power station.

As an alternative to the use of the pressure sensitive sensors 8, the presence of loaded coal wagons can be detected by means of photo-electric devices which response to an identifying marker which is placed on loaded coal wagons.

We claim:

1. Apparatus for measuring the ash content of coal contained in a transport container, said apparatus comprising means for irradiating a known quantity of coal in a transport container with a known dose of thermal neutrons, means for detecting γ-rays having a predetermined energy emitted by the irradiated coal, the γ-rays arising from the capture of thermal neutrons by $^{27}$Al present in the coal, means for producing a signal related to the intensity of the γ-ray emission from the irradiated coal, and means responsive to the said signal to provide an indication of the concentration of the $^{27}$Al in the coal, thereby providing a measure of the ash content of the coal.

2. Apparatus according to claim 1, wherein there is provided means responsive to the said signal to isolate transport containers containing coal the ash content of which exceeds a specified level.

3. Apparatus according to claim 1, wherein there is included means for ensuring that the neutron irradiating means is only operative when a transport container containing coal is in a position for the coal to be in the path of neutrons emitted by the neutron irradiating means.

4. Apparatus according to claim 3, wherein the means for ensuring that the neutron irradiating means only is operative when a transport container is in a position for the coal to be irradiated by neutrons emitted by the neutron irradiating means comprising at least one pressure-sensitive device which is adapted to produce an actuating signal when a load corresponding to a coal-containing transport container passes over it, and means for activating the neutron emitting means in response to the actuating signal.

5. Apparatus according to claim 3, wherein the means for ensuring that the neutron irradiating means only is operative when a coal-containing transport wagon is in a position for the coal to be irradiated by neutrons emitted by the neutron irradiating means comprises a photoelectric device adapted to produce an actuating signal in response to the presence of a loaded transport container, and means for actuating the neutron emitting means in response to the actuating signal.

6. Apparatus according to claim 4, wherein the neutron source is energised in response to the actuating signals to cause it to emit neutrons.

7. Apparatus according to claim 4, wherein the neutron irradiating means includes a continuously operating neutron source the shielding of which is reduced in an appropriate direction in response to the actuating signals, thereby to cause a beam of neutrons to be emitted in that direction.

8. Apparatus according to claim 7, wherein the neutron source is moved bodily from a position in which it is completely shielded to one in which it is only partially shielded thereby to cause the emission of neutrons from the neutron irradiating means.

9. Apparatus according to claim 7, wherein the neutron source includes $^{252}$Cf.

10. Apparatus according to claim 7, wherein said neutron source includes $^{241}$Am/Be.

11. Apparatus according to claim 1, wherein there is provided means for measuring the background intensity of γ-rays having the same energy as those emitted by $^{28}$Al.

12. Apparatus according to claim 1, wherein the γ-ray detecting means is arranged to detect and measure the intensity of γ-rays having an energy of 1.78 MeV arising from subsequent decay of the $^{28}$Al produced by the transformation of $^{27}$Al present in the coal to $^{28}$Al.

13. Apparatus according to claim 11, wherein the neutron source comprises a charged-particle neutron generator tube arranged to produce neutrons having an energy in the region of 14 MeV.

14. Apparatus according to claim 1, wherein there is provided means for determining the bulk density of the coal.

15. Apparatus according to claim 14, wherein there is provided means for measuring the intensity of prompt γ-rays having an energy of 2.23 MeV arising from thermal neutron capture by hydrogen present in the coal thereby to provide an indication of the bulk density of the coal.

16. Apparatus according to claim 1, wherein the γ-ray detecting means is arranged to detect and measure γ-rays arising from a plurality of ash-forming elements in the coal.

17. Apparatus according to claim 1, wherein the transport container is a railway wagon.

18. Apparatus for measuring the ash content of coal contained in wagons forming part of a train comprising means situated at the trackside and arranged to irradiate coal contained in the wagons with a known dose of thermal neutrons through the sides of the wagons, a first γ-ray detector means situated a known distance downline of the irradiating means, a second γ-ray detector situated the same distance up-line of the irradiating means the first and second γ-ray detectors being arranged to measure the intensities of γ-rays of a predetermined energy arising from neutron capture by $^{27}$Al present in the coal, the output from the first γ-ray detector being used to provide a measuring signal and that from the second γ-ray detector being used to provide a measure of the background level of the γ-rays of the predetermined energy, means for ensuring that the neutron irradiating means only operates when a loaded wagon is in an operative position, means for measuring the velocity of the wagons past the neutron irradiating means, and means for deriving an indication of the ash content of the coal in each wagon from the intensity of the said γ-rays.

* * * * *